United States Patent
Cheng et al.

(10) Patent No.: US 6,525,208 B1
(45) Date of Patent: Feb. 25, 2003

(54) EPOXIDATION OF OLEFINS

(75) Inventors: Chi Hung Cheng, Baton Rouge, LA (US); Gerald M. Sulzer, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 10/116,508

(22) Filed: Apr. 3, 2002

(51) Int. Cl.$^7$ .................................. C07D 301/12
(52) U.S. Cl. .................... 549/531; 549/523; 549/524
(58) Field of Search ................... 549/531, 523, 549/524

(56) References Cited

U.S. PATENT DOCUMENTS

| | | | |
|---|---|---|---|
| 2,833,788 A | 5/1958 | Skinner et al. | 260/348.5 |
| 3,644,497 A | 2/1972 | Mesich | 260/497 R |
| 3,708,506 A | 1/1973 | Brunie et al. | 260/348.5 L |
| 3,832,363 A | 8/1974 | Fetterly et al. | 260/348.5 V |
| 4,303,586 A | 12/1981 | Schirmann et al. | 260/348.31 |
| 4,303,587 A | 12/1981 | Schirmann et al. | 260/348.31 |
| 4,476,314 A | 10/1984 | Kuriyama et al. | 549/531 |
| 4,562,276 A | 12/1985 | Venturello et al. | 556/20 |
| 4,562,299 A | 12/1985 | Venturello et al. | 568/811 |
| 4,595,671 A | 6/1986 | Venturello et al. | 502/159 |
| 5,274,140 A | 12/1993 | Venturello et al. | 549/531 |
| 5,324,849 A | 6/1994 | Bonsignore et al. | 556/14 |
| 5,344,946 A | 9/1994 | Warwel et al. | 549/531 |
| 5,780,655 A | 7/1998 | Shum | 549/531 |
| 6,051,725 A | 4/2000 | Crivello et al. | 549/524 |

OTHER PUBLICATIONS

Abstract of DE 19929196, issued 12/00, from Espa@cenet.
Hori et al., "Synthetic Applications of Arylselenenic and Arylseleninic Acids, Conversion of Olefins to Allylic Alcohols and Expoxides", J. Org. Chem, vol. 43, No. 9, 1978, ppg 1689–1697.
Payne et al., "Reactions of Hydrogen Peroxide. IV. Sodium Tungstate Epoxidation of a,b–Unsaturated Acids", J. Org. Chem., 1959, vol.24, ppg 54–55.
Venturello et al., "A New, Effective Catalytic System for Epoxidation of Olefins by Hydrogen Peroxide Under Phase–Transfer Conditions", J. Org. Chem., 1983, vol. 48, No. 21, ppg 3831–3833.
Venturello et al., "Quaternary Ammonium Tetrakis(diperoxotungsto)phosphates(3–)as a New Class of Catalysts for Efficient Alkene Epoxidation with Hydrogen Peroxide",J. Org. Chem., 1988, vol. 53, No. 7, ppg 1553–1557.
Venturello et al., "A Convenient Catalytic Method for the Dihydroxylation of Alkenes by Hydrogen Peroxide", Communications, 1989, ppg 295–297.

*Primary Examiner*—Ba K. Trinh
(74) *Attorney, Agent, or Firm*—Philip M. Pippenger (57) ABSTRACT

Mixed together are (i) hydrogen peroxide; (ii) 1-alkene; (iii) quaternary ammonium salt wherein at least one of the substituents contains at least six carbon atoms; (iv) boric acid, or both a 1,2-diol and boric acid; and (v) a preformed catalyst solution formed from hydrogen peroxide, at least one aqueous inorganic acid, and at least one tungstate salt, while water is continuously removed, such that a 1,2-epoxide is formed. A new method for purifying 1,2-epoxyalkanes is also described.

60 Claims, 2 Drawing Sheets

Figure 1. Batch Reactor System

Figure 2. Continuous Reaction/Distillation System

EPOXIDATION OF OLEFINS

TECHNICAL FIELD

This invention relates to new process technology for the production of epoxides from olefins. More particularly this invention relates to the epoxidation of olefins using a new catalytic system.

BACKGROUND

It is known in the art that olefins can be oxidized to their respective epoxides with hydrogen peroxide in the presence of a peroxotungstate catalyst; see e.g., U.S. Pat. No. 5,274,140 to Venturello et al. (two-phase system), and U.S. Pat. No. 5,780,655 to Shum (single-phase system). It is also known that tungsten compounds are poor catalysts for epoxidation of isolated olefins with aqueous $H_2O_2$ in monophasic systems unless water is continuously removed. See in this connection, Venturello et al., *J. Org. Chem.* 1983, 48, 3831, which cites Payne et al., *J. Org. Chem.* 1959, 24, 54, Hori et al., id., 1978 43, 1689, and Pralus et al., *Fundamental Research in Homogeneous Catalysis*, M. Tsutsui, ed., Plenum, New York, 1979, Vol. 3, pp. 327–343 and references therein.

Other activities on catalytic epoxidation of olefinic compounds include, for example, work reported in U.S. Pat. Nos. 4,303,586, 4,303,587, 4,562,276, and 4,595,671, and in Venturello et al., *J. Org. Chem.*, 1988, 53, 1553 and Venturello et al., *Synthesis Communications*, 1983, 295.

Heretofore azeotropic distillation has been utilized in connection with a single-phase reaction mass in order to continuously remove water so as to maintain a single organic phase in the reaction mass. In particular, a catalyst system was prepared by adding $Na_2WO_4 \cdot 2H_2O$, $H_2SO_4$, and a quaternary ammonium halide to 1-hexene, and heating this mixture while stripping off water from the mixture. Then, concentrated aqueous hydrogen peroxide was added to the resultant mixture, whereby a peroxotungstate catalyst was formed in situ, which catalyzed exothermic epoxidation of 1-hexene to 1,2-epoxyhexane. During the reaction, water and organics were continuously azeotropically stripped from the reactor, so that a single organic liquid phase was maintained in the reactor. The organic portion of the distillate was separated from the water, and recycled to the reactor. The reaction was discontinued when the epoxide concentration in the reactor reached a desired level in the range of 40–50 weight percent. While satisfactory results were achieved this way, it would be desirable to have a longer-lived catalyst that maintains the high selectivity of the reaction.

SUMMARY OF THE INVENTION

This invention provides tungsten-catalyzed epoxidation processes having a longer-lived catalyst that maintains the high selectivity of the reaction.

It has been found that the inclusion of boric acid and an alkanediol in a tungsten-based catalyzed epoxidation reaction, preferably a peroxotungstate-catalyzed epoxidation reaction, prolongs the life of the catalyst while improving the selectivity of the catalyst and suppressing peroxide decomposition.

In one of its embodiments this invention provides a process of forming an epoxide, which process comprises epoxidizing in the liquid phase, an olefinic compound (preferably an olefinic hydrocarbon), with hydrogen peroxide in the presence of a catalytic quantity of a tungsten-based catalyst system (preferably a peroxotungstate catalyst system), wherein (i) boric acid and (ii) at least one alkanediol individually and/or as a reaction product of (i) and (ii) are being or have been included in the liquid phase.

Another embodiment is a process of forming an epoxide, which process comprises:

A) continuously feeding aqueous hydrogen peroxide solution into a reaction mixture formed from components comprising at least one olefinic hydrocarbon to which have been added (i) tungstic acid and/or a tungsten compound, preferably a tungsten (VI) compound, and an inorganic acid, (ii) an onium compound, preferably a quaternary ammonium compound, (iii) boric acid and (iv) at least one alkanediol and/or (v) a borate ester-containing mixture formed from boric acid and at least one alkanediol, such that at least one epoxide is formed; and B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase.

A preferred embodiment is a process of forming an epoxide, which process comprises:

A) continuously cofeeding (1) aqueous hydrogen peroxide solution and (2) at least one olefinic hydrocarbon, into a reaction mixture formed from components comprising (a) at least one olefinic hydrocarbon (b) a tungsten compound, preferably (i) tungstic acid and/or (ii) a tungsten (VI) compound and an inorganic acid, (c) an onium compound, preferably a quaternary ammonium compound, and (d) boric acid and (e) at least one alkanediol and/or (f) a borate ester-containing mixture formed from boric acid and at least one alkanediol, such that at least one epoxide is continuously being formed; and B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase.

These and other embodiments and features of the invention will become still further apparent from the ensuing description and appended claims.

FURTHER DETAILED DESCRIPTION

The processes of this invention comprise mixing hydrogen peroxide, preferably in the form of a concentrated aqueous hydrogen peroxide solution, with at least one olefinic hydrocarbon, preferably a 1-alkene, in the presence of a novel tungsten-based catalyst system in an essentially single phase liquid reaction mixture. The novel tungsten-based catalyst system is either preformed or formed in situ by mixing together a tungsten compound (preferably a tungsten (VI) compound), an inorganic acid, optionally but preferably an onium compound (preferably a quaternary ammonium salt), boric acid, an alkanediol, and hydrogen peroxide. Instead of (or in addition to) using a tungsten (VI) compound and an inorganic acid, tungstic acid can be used. Also, the boric acid and alkanediol can be premixed whereby one or more borate esters are formed. In either case, the catalyst system, whatever its actual composition may be, is present in the liquid phase reaction mixture prior to or shortly after initiating the feed of hydrogen peroxide. Before and during the epoxidation reaction, water is continuously or substantially continuously removed from the reaction mixture by distillation so that an essentially single-phase liquid reaction mixture is maintained during the reaction. Preferably, the alkanediol used in forming the catalyst is a 1,2-alkanediol, most preferably 1,2-hexanediol. In a preferred embodiment wherein an onium compound is used, the onium compound is a quaternary ammonium salt in which at least one of the substituents on the nitrogen atom is an alkyl group containing at least six carbon atoms.

A preferred embodiment of this invention is a continuous epoxidation process which comprises concurrently, or substantially concurrently, feeding into a reaction zone containing a tungsten-based catalyst system, as described above, (A) hydrogen peroxide, preferably in the form of concentrated aqueous hydrogen peroxide solution, and (B) at least one olefinic hydrocarbon, preferably a 1-alkene. During all or substantially all of the time the feeding of (A) and (B) is occurring, the reaction zone is maintained under reflux conditions, such that water, epoxide product, unreacted olefinic hydrocarbon, and some reaction byproducts are continuously or substantially continuously removed from the reaction zone in the form of a vapor stream. The epoxide can be recovered in different ways. In one embodiment, the organic phase is separated from the water phase of the condensed vapor stream, and the epoxide is distilled from the organic phase, by batch or continuous distillation. The olefinic hydrocarbon is isolated and returned to the reaction zone. In another embodiment, which is preferred, the epoxide is recovered by feeding the vapor stream to a distillation column, where the overhead distillate is composed of the olefinic hydrocarbon and water. The olefinic hydrocarbon is separated from the water by means of a liquid-liquid phase separation, and is returned to the reaction zone. The epoxide is recovered as bottoms from the distillation column. This latter recovery procedure is preferred because it eliminates the need to condense the epoxide before its final separation and thus is less energy-intensive, and requires lower capital and operating costs.

The chemical composition of the novel tungsten-based catalyst systems of this invention is not known. What is known however is that whatever the actual composition may be, it is very effective as an epoxidation catalyst. Also this invention makes it possible to provide catalyst systems that retain their effectiveness for extended periods of time.

A variety of tungsten-based epoxidation catalysts can be used in forming the catalyst systems of this invention. These tungsten-based epoxidation catalysts include those described for example in U.S. Pat. Nos. 5,274,140; 5,324,849; or 5,780,655, the full disclosures of which are incorporated herein by reference. These catalysts are improved pursuant to this invention by including or using therewith boric acid and alkanediol and/or a boric acid ester composition formed from boric acid and alkanediol. Other catalyst systems which can be used in the practice of this invention are the tungsten-based catalysts containing phosphorus or arsenic that are described by Venturello and coworkers in various references such as U.S. Pat. Nos. 4,562,276; 4,562,299; *J. Org. Chem.*, 1983, 48, 3831–3; and *J. Org. Chem.*, 1988, 53, 1553–7, the full disclosures of which are incorporated herein by reference, and with which are included or used boric acid and alkanediol and/or a boric acid ester composition formed from boric acid and alkanediol pursuant to this invention. These latter patents refer to such precursor catalyst (of course in the absence of the boric acid and alkanediol and/or a boric acid ester composition formed from boric acid and alkanediol) by the formula $$Q_3XW_4O_{24-2n}$$

where Q is an onium $(RR_1R_2R_3M)^{\oplus}$ cation in which M is chosen from amongst N, P, As, and Sb, and R, $R_1$, $R_2$, and $R_3$ are the same or different, and represent hydrogen atoms or hydrocarbon groups having a total of from 20 to 70 carbon atoms; X is an atom of P or As; and n is an integer from amongst 0, 1 and 2.

It appears that the nomenclature used in describing the known precursor tungsten-based catalysts in the foregoing references is not uniform or standardized. Nevertheless without desiring to be bound by theory it appears reasonable to consider that these precursor catalyst components when used with peroxide yield peroxotungsto or peroxotungstate catalysts which typically include phosphorus, arsenic, antimony, or ammonium species. Thus for convenience the tungsten-based catalysts are sometimes referred to collectively herein as peroxotungstate catalysts, and the catalysts of this invention which are formed by modifying or improving the known peroxotungstate catalysts by inclusion or use therewith of boric acid and an alkanediol, and/or a boric acid ester composition formed from boric acid and alkanediol, are sometimes referred to collectively herein as the catalysts of this invention.

A variety of tungsten compounds can be used in making the catalysts of this invention, such as for example, $WO_2$, $W_2O_5$, $WO_3$, $WS_2$, $WS_3$, $WCl_2$, $WCl_4$, $WCl_5$, $WCl_6$, $WBr_2$, $WBr_5$, $WBr_6$, $WI_2$, $WI_4$, $WOCl_4$, $WO_2Cl_2$, $WOBr_4$, $WO_2Br_2$, $W(CO)_6$, and the like. Preferred are tungsten (VI) compounds, especially salts of tungstate $(WO_4^{2-})$. Examples of suitable tungstate salts include but are not limited to lithium tungstate, sodium tungstate, potassium tungstate, cesium tungstate, magnesium tungstate, calcium tungstate, barium tungstate, ammonium tungstate, cadmium tungstate, cerium tungstate, cobalt tungstate, copper tungstate, and silver tungstate. Preferred tungstate salts are alkali metal tungstates and alkaline earth tungstates. Highly preferred tungstates are sodium tungstate and potassium tungstate. Mixtures of such tungstates can be used.

Inorganic acid is typically added to convert the tungstate salt to its acid form. The amount of acid used is somewhat dependent on the nature of the tungstate salt chosen. It is sometimes advantageous to use slightly excess acid. For example, when sulfuric acid and sodium tungstate are used, the mole ratio of the acid to tungstate is preferably in the range of about 1:1 to about 1:3. Other inorganic acids suitable for use include, but are not limited to, sulfurous acid, nitric acid, nitrous acid, phosphoric acid, hydrochloric acid, hydrobromic acid, and hydroiodic acid. More than one aqueous inorganic acid may used in making the preformed catalyst solution.

Sources of phosphorus or antimony that, optionally, can be used in forming tungsten-based catalyst precursors for use in the practice of this invention include $P_2O_5$, $As_2O_5$, $PCl_5$, $AsCl_5$, $POCl_3$, $AsOCl_3$, or polyphosphoric acid, or water-soluble salts containing P and W or As and W, such as salts of phosphotungstic acid or arsenotungstic acids. Optionally but preferably an onium compound can be used in forming the catalyst systems of this invention. Suitable onium compounds are quaternary salts of the formula:

Where M is N, P, As, or Sb; X is a stable inorganic anion such as $Cl^{\ominus}$, $HSO_4^{\ominus}$, $NO_3^{\ominus}$, etc.; and $R_1$, $R_2$, $R_3$, and $R_4$ are, independently, hydrogen atoms or hydrocarbyl groups providing a total number of carbon atoms of up to about 70, and preferably in the range of about 8 to about 50, and more preferably in the range of about 18 to about 50 carbon atoms. Most preferred as a group are the quaternary ammonium compounds, and of these quaternary ammonium salts in which at least one of the hydrocarbyl substituents on the nitrogen atom contains at least six carbon atoms are preferred. More preferably, three of the substituents on the nitrogen atom contain at least six carbon atoms per substituent; still more preferably, each of the three substituents contains 6 to about 16 carbon atoms, and the remaining substituent is ethyl, or more preferably methyl. Tetraalkylammonium compounds having one methyl or ethyl group and three alkyl groups which contain, independently, in the range of 6 to about 12 carbon atoms are another preferred group. Especially preferred are tetraalkylammonium halides in which two or three of the alkyl groups substituents on the nitrogen atom each contain independently in the range of 6 to about 12 carbon atoms and each of the one or two other alkyl substituents on the nitrogen atom is independently a methyl or ethyl group. The anion portion of the quaternary ammonium salt can be any of a number of inorganic anions, including nitrate, nitrite, borate, chloride, bromide, and iodide. Chloride and bromide are preferred inorganic anions; thus, the quaternary ammonium salt is preferably a chloride or bromide salt. Examples of quaternary ammonium salts that can be used include, but are not limited to, hexyltrimethylammonium chloride, dihexyldimethylammonium bromide, hexyl-octyldiethylammonium chloride, dihexyloctylmethylammonium chloride, trioctylethyl-ammonium bromide, tricaprylylmethylammonium chloride, and tridodecylmethylammonium bromide. Preferred quaternary ammonium salts are such tetraalkylammonium halides as methyl(tri-n-octyl)-ammonium chloride, methyl(tri-n-octyl) ammonium bromide, ethyl(tri-n-octyl)ammonium chloride, ethyl(tri-n-octyl)ammonium bromide, di(hexyl)(octyl) methyl-ammonium chloride, di(hexyl)(octyl) methylammonium bromide, tri(dodecyl)methyl-ammonium chloride, or tri(dodecyl)methylammonium bromide. Mixtures of quaternary ammonium salts can be used. The mole ratio of the ammonium salt to tungstate salt is preferably in the range of about 0.5:1 to about 1.5:1, and more preferably in the range of about 0.8:1 to about 1.2:1.

Boric acid in solid form or aqueous solutions of boric acid can be used. When aqueous solutions of boric acid are used, the water is subsequently removed by distillation. Preferably, the mole ratio of boric acid to tungstate salt is in the range of about 2:1 to about 20:1. More preferably, the mole ratio of boric acid to tungstate salt is in the range of about 15:1 to about 20:1.

The alkanediol employed in the practice of this invention can be a straight-chain or branched chain compound. Preferably, but not necessarily, at least one of the hydroxyl groups is on a terminal carbon atom. A few non-limiting examples of suitable diols include 2,3-butanediol, 2,4-pentanediol, 1,3-propanediol, 1,3-butanediol, and 2-methyl-1,3-propanediol. More preferred are 1,2-alkanediols which can be a straight-chain diol or a branched 1,2-diol, with the straight-chain 1,2-diols being more preferred. Regardless of its structure, the alkanediol preferably contains about 3 to about 12 carbon atoms, more preferably in the range of about 5 to about 10 carbon atoms, and still more preferably in the range of 5 to 8 carbon atoms. Non-limiting examples of suitable preferred 1,2-alkanediols include 1,2-propanediol, 2-methyl-1,2-propanediol, 1,2-butanediol, 1,2-pentanediol, 4-methyl-1,2-pentanediol, 1,2-hexanediol, 3-ethyl-1,2-hexanediol, 1,2-heptanediol, 1,2-octanediol, 1,2-nonanediol, 1,2-dodecanediol, and the like. More preferred diols are 1,2-pentanediol, 1,2-hexanediol, 1,2-heptanediol, and 1,2-octanediol, and of which 1,2-hexanediol is especially preferred. It is also preferred to select the diol that corresponds to the 1-alkene chosen; e.g., if 1-hexene is the 1-alkene, the most preferred diol is 1,2-hexanediol. This eases the workup done after the process of the invention has been performed. Although not preferred, mixtures of diols may be used in the practice of this invention. The mole ratio of 1,2-alkanediol to tungstate salt is preferably in the range of about 15:1 to about 30:1.

Hydrogen peroxide used to make the preformed catalyst solution may be neat or an aqueous solution. Again, aqueous solutions are preferred for safety reasons. The concentration of hydrogen peroxide in the aqueous solution can be quite low, e.g., 5–10 wt %, but is preferably in the range of about 30 wt % to about 80 wt %; and more preferably in the range about 50 wt % to about 75 wt %. Concentrations of hydrogen peroxide toward the higher end of the range, i.e., closer to 75 wt %, e.g., about 70 wt %, are highly preferred.

In forming the boron-modified catalysts and carrying out the epoxidation, boric acid and diol can be mixed together with the quaternary ammonium salt, the preformed catalyst solution, and the 1-alkene in any order.

Without wishing to be bound by theory, and as noted above, it is believed that contacting the components of the preformed catalyst solution produces a peroxotungstate compound, which acts as a catalyst for the formation of the epoxide.

Various epoxidizable olefinic compounds can be epoxidized in the practice of this invention. Examples include aromatic or cycloaliphatic hydrocarbons containing one or more epoxidizable olefinic ring substituents. Styrene, divinylbenzene, and vinylcyclohexane serve as non-limiting specific examples of such compounds. Preferred however are 1-alkene hydrocarbons. These can be a straight-chain 1-alkene or a branched 1-alkene; straight-chain alkenes are preferred. The alkene preferably contains about four to about twelve carbon atoms. Suitable alkenes include 1-propene, 2-methyl-1-propene, 1-butene, 1-pentene, 4-methyl-1-pentene, 1-hexene, 3-ethyl-1-hexene, 4-n-propyl-1-heptene, 1-octene, 1-nonene, 1-unadecene, 1-dodecene, 5-methyl-1-dodecene, 1-tetradecene, 1-hexadecene, and the like. Preferred alkenes are 1-pentene, 1-hexene, 1-heptene, and 1-octene; highly preferred is 1-hexene. Though not preferred, mixtures of alkenes may be used in the practice of this invention. The possibility of epoxidizing functionally-substituted olefins using the catalysts of this invention has not escaped our attention, and is deemed entirely feasible. Examples of such functionally-substituted compounds are given in some of the references incorporated herein by reference, as well as in other references in the prior art.

In conducting the epoxidation, hydrogen peroxide may be used neat or as an aqueous solution. For safety reasons, it is preferred to use an aqueous solution of hydrogen peroxide. The concentration of hydrogen peroxide in the aqueous solution can be in the range of about 5 to about 80 wt %, but is preferably in the range of about 30 wt % to about 75 wt %; and more preferably in the range about 50 wt % to about 70 wt %. Such higher concentrations of hydrogen peroxide are preferred because they minimize the amount of water introduced to the reaction mixture.

Water is present in the epoxidation reaction as a reaction product, and is also introduced with hydrogen peroxide and the preformed catalyst solution. Because a single, predominantly organic phase is desired for the epoxidation reaction, water is removed during the process. This is preferably done by distillation. Removal of the water minimizes undesired side reactions.

A more preferred mode of operation is the mixing of all of the components except the hydrogen peroxide, heating the mixed components to reflux, and then mixing the hydrogen peroxide; more highly preferred is the continuing of reflux conditions during the entire mixing of the hydrogen peroxide. A highly preferred way of practicing the invention is the mixing of the alkene and ammonium salt; mixing them with the preformed catalyst solution and boric acid; heating this mixture to reflux; and then mixing the hydrogen peroxide while maintaining reflux conditions. It is also preferred to remove the produced epoxide, preferably by distillation.

The epoxidation reaction of this invention can, and preferably is, conducted in continuous mode. It is preferred to conduct the process so that the volume of the contents of the reactor and the volume of the portion of the product mixture removed from the reactor are equal or substantially equal whereby the volume of reactor contents remains constant or substantially constant. In this way, reactors with smaller volumes can be employed. Thus, once steady-state conditions have been achieved in a continuous reactor, the separate feeds can be fed in appropriate proportions on a continuous basis, and the reactor contents maintained under the appropriate reaction conditions. Additionally, the per catalyst use can be maximized, in the sense that replacement catalyst solution need not be added until that already present in the reaction zone shows signs of degradation.

It is preferred to discharge the entire reaction mass when heavy by-products in the reactor accumulate to an acceptable level over time. Alternatively a continuous purge can be used to remove such by-products.

When a continuous process is started, the preformed catalyst solution and the quaternary ammonium salt and the boric acid and 1,2-diol and some alkene are present in the reaction zone prior to the initial feeding of the hydrogen peroxide and 1-alkene. It is also preferred that the hydrogen peroxide and 1-alkene are fed concurrently. If the amount of one feed or the other is greater, the reaction will not be adversely affected, nor will the degradation of the catalyst be accelerated.

During all or substantially all of the time that both the 1-alkene and the hydrogen peroxide are being fed, reflux conditions are maintained in the reaction zone. Both water and the epoxide that is formed are removed from the reaction zone during the epoxidation reaction; both are preferably removed by distillation. Because water is continually formed during the epoxidation reaction, continuous or substantially continuous removal of the water from the reaction zone is necessary in order to maintain a single, predominantly organic phase in the reaction zone. The epoxide is preferably removed continuously or substantially continuously from the reaction zone.

In order to operate in continuous mode for long periods of time, the catalyst occasionally needs to be replenished. This is easily and preferably accomplished by intermittently adding more of the preformed catalyst solution to the reaction zone.

The processes of this invention, whether performed in a batch mode, semi-batch mode, or continuous mode, are preferably conducted so that such things as the feeds, reaction, and maintenance of reflux conditions occur "continuously" during the reaction. However, it cannot be stressed strongly enough that one must not gain the impression that inconsequential interruption in one or more of such things cannot occur. Interruptions which do not materially affect the conduct of the process are not excluded from the scope of this invention. To safeguard against hypertechnical legalistic word interpretation, it has been deemed prudent to employ terms such as "substantially continuously" in describing this invention. But whatever the terms used, the process should be conducted as one of ordinary skill in the art would carry out the processes after a thorough, unbiased reading of this entire disclosure and in keeping with the spirit of the invention gained from such a reading.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there may be one or two different time intervals between or among the respective feeds, again provided that the time intervals are of sufficiently short duration to cause no material adverse effect upon the overall process.

For a batch run or for an initial charge to a reaction zone in a continuous process, the mole ratio of ammonium salt to 1-alkene is preferably in the range of about 1:500 to about 1:1500, and more preferably is in the range of about 1:800 to about 1:1000. In a continuous process, when the quaternary ammonium salt needs to be replenished, due to decomposition in the reactor, the ammonium salt can be mixed with the alkene or can be intermittently added with the preformed catalyst solution, such that the optimal catalytic activity and selectivity are maintained.

While the use of equimolar or nearly equimolar amounts of 1-alkene or hydrogen peroxide may be desirable, either the 1-alkene or the hydrogen peroxide can be used as the reagent in excess without adverse effect on the process.

For the purification of one or more 1,2-epoxyalkanes (i.e., 1,2-epoxides), at least one inorganic base, at least one hydride source, and at least one 1,2-epoxyalkane are mixed together. These ingredients can be mixed together in any order. It is preferred to use the inorganic base as an aqueous solution. Also preferred is the use of the hydride source as an aqueous solution. Most preferred is a single aqueous solution of both the inorganic base and the hydride source, which is then mixed with the 1,2-epoxyalkane. The treatment can be conducted at ambient to moderately elevated temperature, preferably at 5–60° C.

Various inorganic bases may be used in the purification. Such inorganic bases include oxides, hydroxides, carbonates, and bicarbonates of the alkali metals, alkaline earth metals, zinc, and the like. Examples of suitable bases are sodium oxide, potassium oxide, magnesium oxide, calcium oxide, zinc oxide, lithium hydroxide, sodium hydroxide, potassium hydroxide, rubidium hydroxide, magnesium hydroxide, calcium hydroxide, barium hydroxide, zinc hydroxide, lithium bicarbonate, sodium carbonate, potassium bicarbonate, rubidium carbonate, magnesium carbonate, calcium carbonate, and zinc carbonate. Alkali metal bases are preferred; more preferred are alkali metal hydroxides, and sodium hydroxide is most preferred as the inorganic base. Mixtures of inorganic bases can be used. The inorganic base may be introduced to the reaction vessel in solid form or as a solution; an aqueous solution of the inorganic base is particularly preferred. When an aqueous solution of inorganic base is used, the concentration of inorganic base in the aqueous solution is preferably in the range of about 2 wt % to about 50 wt %.

For the hydride source, it is recommended that those which are not very water-reactive be chosen, as water will be present in the reaction mixture. Examples of hydride sources that may be used include lithium aluminum hydride, lithium borohydride, sodium aluminum hydride, sodium borohydride, and potassium borohydride. The most preferred hydride source is sodium borohydride.

The 1,2-epoxyalkane to be purified can be from a crude reaction mixture or can be prepurified (i.e., already purified via another method) prior to the use of the purification process of this invention. The 1,2-epoxyalkane can be a straight-chain 1,2-epoxyalkane or a branched 1,2-epoxyalkane; straight-chain epoxyalkanes are preferred. The epoxyalkane preferably contains about four to about twelve carbon atoms. Suitable epoxyalkanes include 1,2-epoxypropane, 2-methyl-1,2-epoxypropane, 1,2-epoxybutane, 1,2-epoxypentane, 4-methyl-1,2-epoxypentane, 1,2-epoxyhexane, 3-ethyl-1,2-epoxyhexane, 1,2-epoxyheptane, 1,2-epoxyoctane, 1,2-epoxynonane, 1,2-epoxydodecane, and the like. Preferred epoxyalkanes are 1,2-epoxypentane, 1,2-epoxyhexane, 1,2-epoxyheptane, and 1,2-epoxyoctane; highly preferred is 1,2-epoxyhexane. Impurities may be removed from mixtures of epoxyalkanes using the described method.

Without wishing to be bound by theory, it is believed that impurities present with 1,2-epoxyalkanes can be reduced by the hydride source. In particular, it is thought that aldehydes and/or ketones, if present, will be converted to alcohols. When the epoxyalkane is to be converted to the corresponding 1,2-alkanediol, this hydride source treatment results in minimization of odors, as compared to epoxyalkanes which are converted to the 1,2-alkanediol without the hydride treatment.

The following examples are presented for purposes of illustration, and are not intended to impose limitations on the scope of this invention.

EXAMPLE 1

Batch Reactions to Form the Epoxide

To a 500-ml Pyrex reactor was first charged a mixture of 1.27 g tricaprylylmethyl-ammonium chloride (2.6 mmol; Aliquat® 336, Aldrich Chemical Company) and 210.2 g 1-hexene (2,498 mmol). For the runs in which 1,2-hexanediol and/or boric acid were used, they were initially added when the Aliquat and 1-hexene solution were added to the reactor. The reactor was then heated, reaching reflux temperature (~64° C.) within 30 minutes. A peroxotungstate solution was prepared by mixing 34.9 wt % $Na_2WO_4.2H_2O$ (2.708 g, 2.86 mmol W), 96.4% $H_2SO_4$ (0.398 g, 3.91 mmol), and 70% $H_2O_2$ (0.90 g, 18.5 mmol) for 2 minutes at room temperature, resulting in a clear peroxotungstate solution. The peroxotungstate solution was then added to the reactor during 11 minutes via a dropping funnel. Following the addition of the peroxotungstate solution, 70% $H_2O_2$ was fed to the reactor over a period of several hours. The peroxide flow rate was slower (~half of the full rate) in the first 30 minutes and maintained at a constant rate afterward. Throughout the reaction, reflux conditions were maintained.

The byproduct water was continuously removed from the reactor by azeotropic distillation to ensure that a single, organic phase was present in the reactor. The aqueous phase was collected in a Dean-Stark trap while the organic phase was continuously refluxed back into the reactor. Oxygen evolution was observed in the oil bubbler. Based on the bubbling rate, 5–10% of the peroxide decomposed to oxygen. The rate of peroxide decomposition was much higher during the first 2 hours. The reaction was stopped after all of the peroxide was fed and the reactor had been heated for an additional 10 minutes. When a top organic phase was present in the Dean-Stark trap, that organic phase was combined with the reaction mass. The organic reaction mass was analyzed by gas chromatography for 1-hexene and 1,2-epoxyhexane. A sample of the reaction mass was extracted with 10× deionized water and the pH of the extract was measured using a pH probe. The pH of the final mixtures ranged from 3.3 to 4.1. The aqueous phase was collected from the Dean-Stark trap and its $H_2O_2$ concentration was determined by titration with $Na_2S_2O_5$ and by using Quantofix $H_2O_2$ test strips (Aldrich Chemical Company). It was assumed that one mole of $Na_2S_2O_5$ can destroy two moles of $H_2O_2$.

All of the batch runs used the same amounts of $Na_2WO_4$, $H_2SO_4$, and 1-hexene. The amounts of 1,2-hexanediol, boric acid, and 70% $H_2O_2$ employed in each run are listed in Table 1. The results for all of the batch runs are summarized in Table 1. The 1,2-epoxyhexane yield is based on the total amount of hydrogen peroxide charged. Runs 1–4 are comparative runs.

TABLE 1

| Run | 1,2-hexanediol (mmol) | B(OH)$_3$ (mmol) | H$_2$O$_2$ Fed (mmol) | H$_2$O$_2$ Feed Time | H$_2$O$_2$ Decomposed | Yield |
| --- | --- | --- | --- | --- | --- | --- |
| 1 | 0.00 | 0.00 | 1379 | 8.0 hr. | 5–10% | 79% |
| 2 | 47 | 0.00 | 684 | 3.8 hr. | <2% | 27% |
| 3 | 8 | 0.00 | 1254 | 7.25 hr. |  | 80% |
| 4 | 0.00 | 22 | 1038 | 6.0 hr. | 5–10% | 66% |
| 5 | 45 | 45 | 1295 | 7.4 hr. | <2% | 89% |
| 6 | 46 | 24 | 289 | 7.3 hr. | <2% | 87% |
| 7 | 8.5 | 8.74 | 1274 | 7.2 hr. |  | 70% |
| 8 | 21 | 10.7 | 1298 | 7.0 hr. |  | 69% |
| 9 | 84 | 43 | 1270 | 7.2 hr. | <2% | 88% |
| 10 | 81 | 51.6 | 1118 | 7.0 hr. |  | 80% |
| 11 | 46 | 45.8 | 1240 | 8.0 hr. |  | 84% |

EXAMPLE 2

Continuous Reactions to form the Epoxide

This Example is comparative.

Run A

Figure 1:
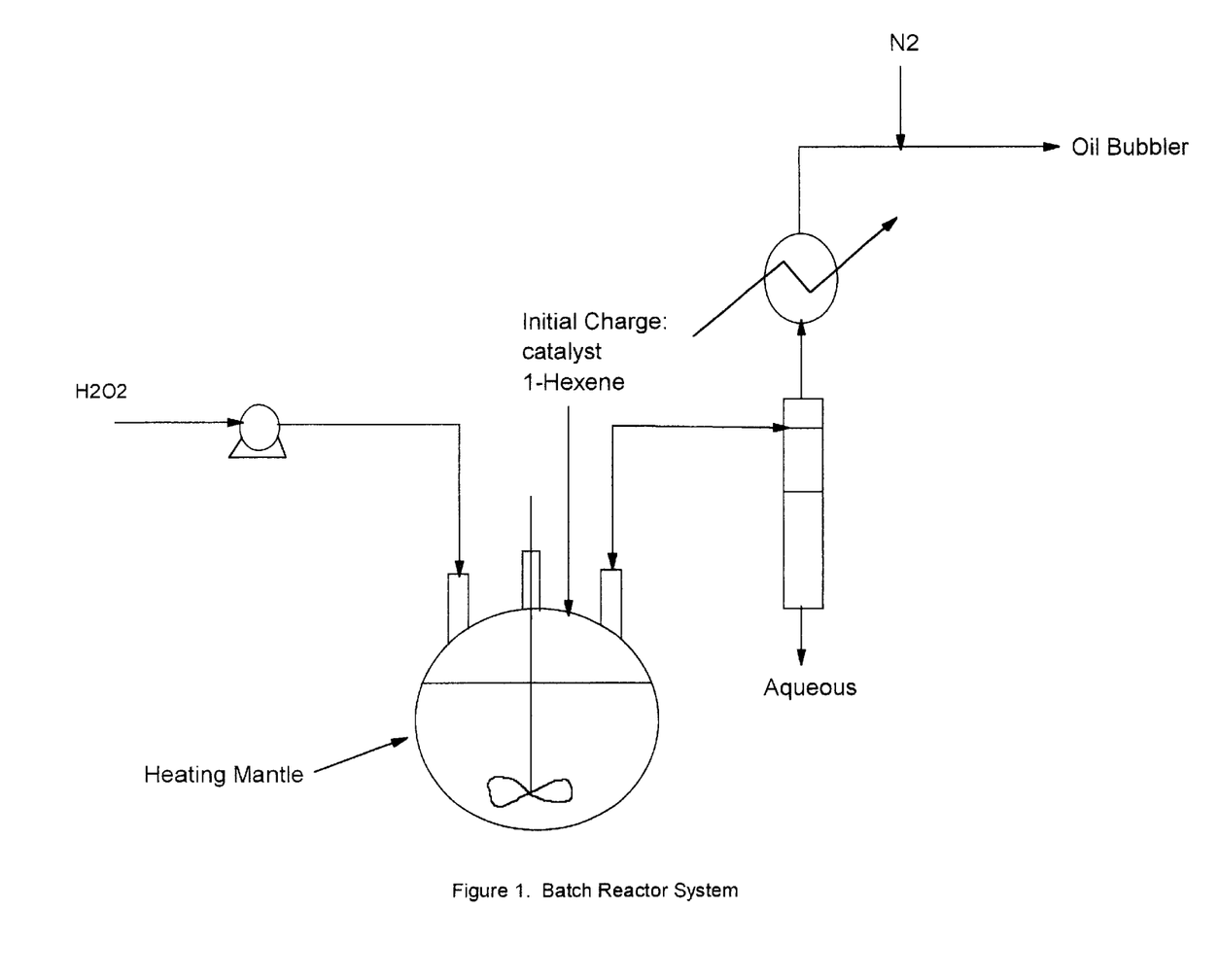
FIG. 1 is a schematic diagram of a batch reactor system suitable for use in the practice of this invention on a laboratory scale.
Figure 2:
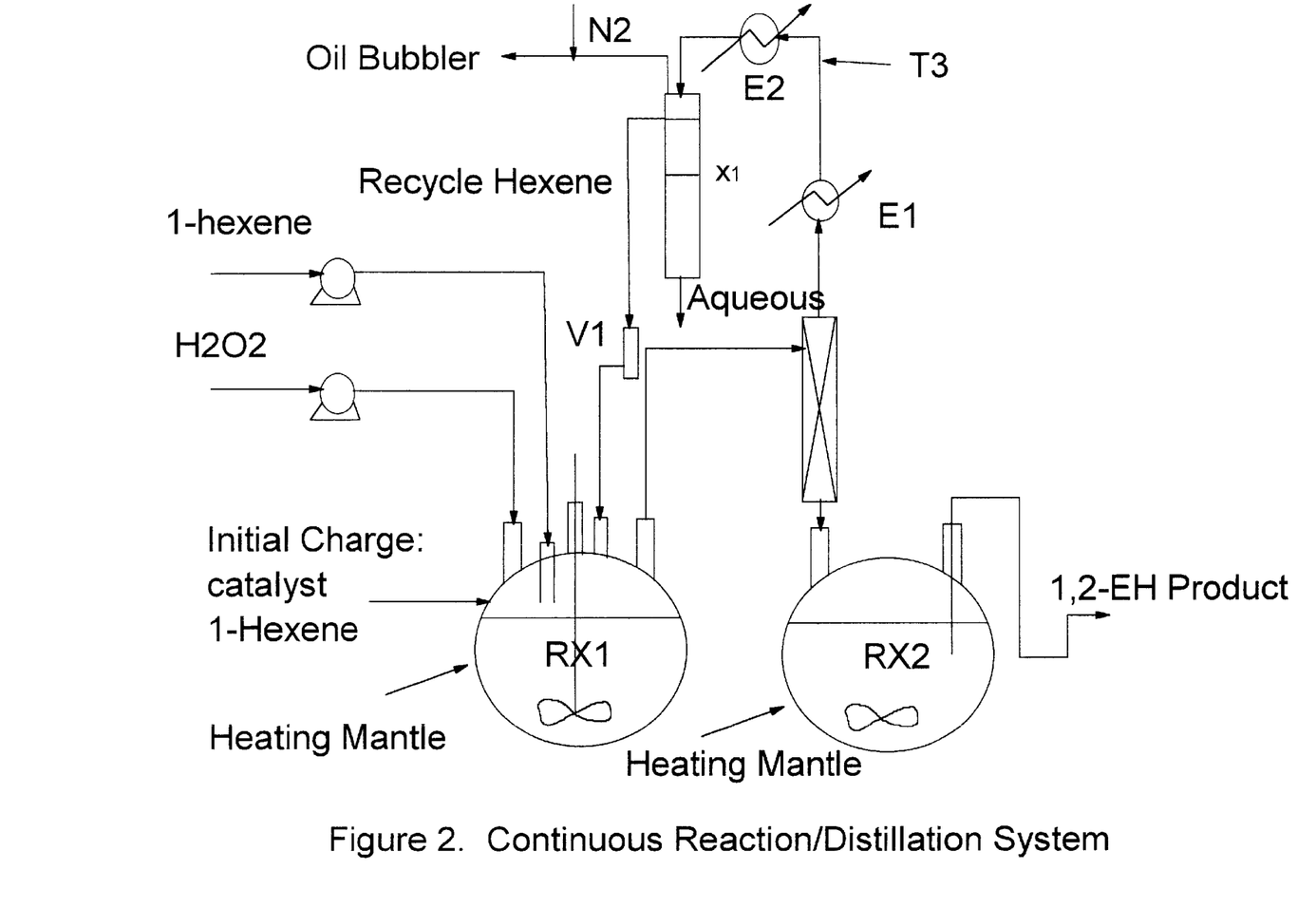
FIG. 2 is a schematic diagram of a continuous reactor system suitable for use in the practice of this invention on a laboratory scale.

A schematic diagram of the continuous reaction system used is given in FIG. 2. 1-Hexene and 70% $H_2O_2$ were continuously fed to the epoxidation reactor (RX1), a 500-mL round bottom pyrex flask. The vapor stream from RX1 was continuously distilled using a 1.25-inch OD and 11-inch long column packed with stainless steel Pro-Pak® packing. The column allowed the continuous separation and removal of the 1,2-epoxyhexane product from the water by-product and recycle 1-hexene.

A peroxotungstate solution is first prepared by stirring a mixture of 3.283 g of 34.89% $Na_2WO_4.2H_2O$ in water, 0.473 g of 96.4% $H_2SO_4$, and 1.13 g of 70% $H_2O_2$. RX1 is initially charged with a solution of 1.272 g of Aliquat® 336, Aldrich Chemical Company) and 210 g of 1-hexene (98%). The column reboiler (RX2) is charged with 65.0 g of 1-hexene. RX1 and RX2 are then heated until boiling. The overhead distillate temperature (T3) was maintained at ~62° C. by an air-cooled partial condenser (E1). The condensate from the overhead total condenser (E2) is fed to a phase separator (X1). The top 1-hexene phase from X1 is continuously overflowed to a 25-mL volumetric flask (V1) and then recycled directly back to RX1. The heat input rate to RX1 is adjusted such that the hexene recycle flow rate is about 5 cc/min. The heat input rate to RX2 is adjusted to maintain a roughly constant level in RX2.

After conditions stabilized, 4.1 g of the above peroxotungstate solution (2.76 mmol of W) is added slowly to the reactor. Then 1.8 g of 70% $H_2O_2$ is fed to RX1 via a peristaltic pump over 30 mins. The peroxide flow rate is then maintained at ~9.2 g/hr. The rate of peroxide decomposition in the initial 3 hours is roughly 5–10%. but decreases to <2% after 4 hours. The aqueous level in X1 is maintained at about 20 mL by continuously purging the aqueous layer to a 25-mL graduater. The $H_2O_2$ level in the aqueous layer is measured by titration with $Na_2S_2O_5$ and with the use of Quantofix peroxide test strips (Aldrich).

Both RX1 and RX2 temperatures start to increase as 1,2-epoxyhexane is formed. When RX2 temperature reaches 121° C., a 0.2% Aliquat in 1-hexene solution is fed continuously to RX1. The flow rate is adjusted slightly during the reaction to maintain roughly constant liquid volume (~275 mL) in RX1. The liquid level in RX2 is maintained roughly constant (~80 g) by continuously purging to the 1,2-epoxyhexane product receiver (P1).

The catalytic selectivity and reactivity are continuously monitored by analyzing samples from RX1, RX2, and the aqueous byproducts. The deactivation of the catalyst is indicated by an increase in the $H_2O_2$ level in the aqueous phase. When this occurs, a makeup peroxotungstate, which contains 23.6% $Na_2WO_4.2H_2O$, 9.68% $H_2SO_4$, and 15.6% $H_2O_2$, is added to the reactor. At 30 hr and 61 hr, 1.4 g (1.0 mmol W) and 1.04 g (0.74 mmol W), respectively, of the makeup peroxotungstate solution is added to the reactor in order to maintain the catalytic activity. The reaction is allowed to continue for a total of 65.5 hours.

After 65.5 hours a total of 603.6 g of 70% $H_2O_2$ (12.4 gmol) and 912 g of 1-hexene (10.8 gmol) were fed. The final reaction heel in RX1 contained 51.4 wt % of 1-hexene, 17.7 wt % of 1,2-epoxyhexane, and 2.4 wt % of 1,2-hexanediol. A total of 1033 g of 1,2-epoxyhexane (10.3 gmol) was produced. The overall 1,2-epoxyhexane yield, based on the $H_2O_2$ charged, was calculated to be 83%.

Run B

Continuous Reaction, with Boric Acid and HD Addition

The reaction was conducted in the same manner as in Run A except that the initial charge to RX1, the RX1 reaction volume, and the peroxide flow rate were increased as given below.

a) Initial charge: 4.04 mmol $Na_2WO_4$, 5.53 mmol $H_2SO_4$, 63.5 mmol 1,2-HD, 63.7 mmol $B(OH)_3$, and 288 g 1-hexene.
b) RX1 volume maintained at: ~350 ml.
c) 70% $H_2O_2$ flow rate: 10.5 g/hr.

The catalyst remained active and selective until after about 61 hours. 0.67 g 34.9% $Na_2WO_4.2H_2O$ (0.7 mmol W) was added to the epoxidation reaction mass after 64 hours and the reaction was allowed to continue for a total of 68 hours. After 68 hours, a total of 710.9 g 70% $H_2O_2$ (14.6 gmol) and 1030 g (12.24) of 1-hexene were fed. The final reaction heel in RX1 contained 48 wt % 1-hexene, 16.2 wt % 1,2-epoxyhexane. A total of 1210 g 1,2-epoxyhexane (12.1 gmol) was produced. The overall 1,2-epoxyhexane yield, based on the the $H_2O_2$ charged was calculated to be 83%.

The 1,2-epoxyhexane used in Examples 3 and 4 was prepared in a manner similar to that described in Run B of Example 2. The crude 1,2-epoxyhexane used in Examples 3 and 4 contained 96.6% 1,2-epoxyhexane, 0.35% 1-hexene, ~0.16% pentanal, ~0.4% 1-hydroxy-2-hexanone, and 0.54% pentanoic acid, as determined by gas chromatography.

EXAMPLE 3

Purification of 1,2-epoxyhexane

This Example is comparative.

Step A. Crude 1,2-epoxyhexane (318.0 g) was placed in a 500-mL separatory funnel. Aqueous NaOH (10 wt %, 31.8g) was charged to the funnel, and the contents of the funnel were mixed well for 5 minutes. The mixture was allowed to settle for approximately 20 minutes and then the phases were separated. The bottom aqueous phase weighed 30.9 g (yellow), and the top organic phase weighed 318.8 g. The organic phase was then washed twice with tap water (31.8 g per wash). The washed organic phase weighed 316.5 g and contained 96.8% 1,2-epoxyhexane, 0.3% 1-hexene, and 0.2% pentanal.

Step B. A 1 liter stainless steel autoclave reactor, equipped with an electrical concentric furnace, thermowell, mechanical agitator, pressure transmitter, and a cooling coil was charged with water (400 g) and $Na_2HCO_3$ (8.00 g). After pressure testing with nitrogen and venting to atmospheric pressure, the reactor was then heated to and maintained at 152° C. During heating, the reactor was periodically vented to remove the inert impurities. 1,2-Epoxyhexane (151.1 g) was then fed at a constant rate to the reactor via a dipleg over 3 hours, and then the reactor was allowed to cook for an additional 30 minutes. The reactor pressure peaked at about 69 psig after about 30 minutes of feeding 1,2-epoxyhexane, but then slowly dropped to 55 psig at the completion of the reaction. The reaction mass (550.9 g) was analyzed by gas chromatography and contained 31% 1,2-hexanediol, 0.3% 1,2-epoxyhexane, and 1.2% dimer.

Step C. A batch distillation column packed with 12" glass Raschig rings and equipped with a round bottom flask and an overhead condenser was used. To the bottom flask was charged most of the above hydrolysis reaction crude (544.2 g). The water from Step B (372.9 g) which contained 2.8% 1,2-hexanediol was distilled at 100 mmHga until the bottom temperature reached 150° C. More 1,2-hexanediol was then recovered in the distillate at 35 mmHga. The bottom temperature increased slowly from about 147° C. to 170° C. The 1,2-hexanediol (142.3 g) was analyzed by GC and contained 98.9% 1,2-hexanediol, 0.1% dimers, 27 ppm pentanal, 4.8 ppm hexanal, and 350 ppm 1,2-epoxyhexane.

Step D. A Pyrex column 20 inches long with a 1.5 inch outer diameter was packed with ¼" SS ProPak® packing. The bottom 1 foot section of the column was heated by a concentric electrical furnace maintained at 131° C. while the top 8" section was heated with electrical heating tape maintained at a surface temperature of about 145° C. Thermocouples were placed in the top, middle, and bottom of the column, and typically read between 100 and 135° C. during operation. A peristaltic pump (Masterflex) fed 1,2-hexanediol to the top of the column at a constant rate of about 4.0 g/min. Nitrogen, maintained at 0.44 scfh by a rotameter, was preheated by the electrical furnace and fed to the bottom of the column. The liquid effluent was collected in the bottom of the column into a round-bottomed flask. The vapor stream was cooled by a water-cooled condenser. After feeding, the column was allowed to drain for about 10 minutes. Typically about 10–20 g of the 1,2-hexanediol remained in the column internals. The overhead distillate typically weighed 2–4% of the 1,2-hexanediol fed. Although it may not be necessary, all 1,2-hexanediol samples prepared in this Example were passed to the column twice.

A total of 140 g of the 1,2-hexanediol distillate was processed. The final product (115 g) was obtained and contained 99.2% 1,2-hexanediol, 0.1% dimer, 7 ppm pentanal, 0.7 ppm hexanal, and 2.2 ppm 1,2-epoxyhexane, as determined by GC. The sample has a grassy odor.

The results of this Example are summarized in Table 6.

TABLE 6

|  | 1,2-epoxyhexane | 1,2-hexanediol | hexene | dimers | pentanal | hexanal |
| --- | --- | --- | --- | --- | --- | --- |
| Step A | 96.8% |  | 0.3% |  |  |  |
| Step B | 0.2 | 31% |  | 1.2% |  |  |
| Step C | 350 ppm | 98.9% |  | 0.1 | 27 ppm | 4.8 ppm |
| Step D | 2.2 ppm | 99.2% |  | 0.1 | 7 ppm | 0.7 ppm |

EXAMPLE 4

Purification of 1,2-epoxyhexane

The procedures used in all runs of this Example were the same as or similar to those employed in Example 3, except that 12% NaBH$_4$ in 40 wt % aqueous NaOH was used instead of 10 wt % aqueous NaOH. Steps B, C, and D of this Example are for analytical purposes only, and do not form part of the invention. Step B of Run iii was performed in a slightly different manner. The amounts of reagents used are shown in Table 7, and the results of the three runs are summarized in Table 8.

In Step B of Run iii, water (397.2 g) and CH$_3$SO$_3$H (0.40 g) were charged to a 1 liter stainless steel autoclave reactor equipped with an electrical concentric furnace, thermowell, mechanical agitator, pressure transmitter, and a cooling coil. After pressure testing with nitrogen and venting to atmospheric pressure, the reactor was then heated to and maintained at 124° C. During heating, the reactor was periodically vented to remove the inert impurities. The 1,2-epoxyhexane was then fed at a constant rate to the reactor via a dipleg over 55 minutes and then the reactor was allowed to cook for an additional 5 minutes. The reactor pressure peaked at about 24 psig after about 5 minutes of feeding 1,2-epoxyhexane, but then slowly dropped to 19 psig at the completion of the reaction. Prior to performing Step C, the reaction mass had its pH adjusted to 7.5 by the addition of an aqueous NaOH solution (2.45 wt %).

The products from all three runs had a significant reduction of the grassy odor noted in the product of Example 3.

TABLE 7

|  | Run i | Run ii | Run iii |
| --- | --- | --- | --- |
| Step A |  |  |  |
| 1,2-epoxyhexane | 149.0 g | 154.3 g | 150.8 g |
| 12% NaBH$_4$ in 40 wt % NaOH (aq.) | 3.77 g | 1.938 g | 3.746 g |
| H$_2$O | 11.5 g | 13.45 g | 12.27 g |
| mixing time | 30 min. |  | 3.5 hr. |
| water for wash | 15.7 g × 2 | 15.7 g | 15.6 g |
| Step B |  |  |  |
| 1,2-epoxyhexane from Step A | 145.1 g | 148.6 g | 145.77 g |
| H$_2$O | 388 g | 400 g |  |
| NaHCO$_3$ | 7.76 g | 8.0 g |  |
| feeding time | 2.4 hr. | 2.5 hr. | 55 min. |

TABLE 7-continued

|  | Run i | Run ii | Run iii |
| --- | --- | --- | --- |
| Step C |  |  |  |
| product mass from Step B | 532.1 g | 528.9 g | 530.4 g* |
| extraction water | 107.9 g | 101.4 g |  |
| Step D |  |  |  |
| product mass from Step C | 145.1 g | 144.6 g | 143.6 g |
| final product | 113.2 g | 116.4 g | 113.3 g |

*Weight of the reaction mass prior to neutralization.

TABLE 8

|        | 1,2-epoxyhexane | 1,2-hexanediol | hexene | dimers | pentanal | hexanal |
|--------|-----------------|----------------|--------|--------|----------|---------|
| Run i | | | | | | |
| Step A | 97.1%   | 0.4%  | 0.3% |      |         |         |
| Step B | 0.6%    | 29.1% |      | 0.7% |         |         |
| Step C | 75.1 ppm| 99%   |      | 0.1% | 3.1 ppm | 2.6 ppm |
| Step D | 2.3 ppm | 99.1% |      | 0.1% | 0.6 ppm | 0.5 ppm |
| Run ii | | | | | | |
| Step A | 96.7%   | 0.5%  | 0.3% |      |         |         |
| Step B | 0.1%    | 28.1% |      | 1.3% |         |         |
| Step C | 0.1%    | 97.7% |      | 0.3% |         |         |
| Step D | 1.7 ppm | 98.4% |      | 0.4% | 1 ppm   | 0.4 ppm |
| Run iii | | | | | | |
| Step A | 96.6%   | 0.5%  | 0.3% |      |         |         |
| Step B | 0.1%    | 28.5% |      | 1.3% |         |         |
| Step C | 0.1%    | 97.7% |      | 0.3% |         |         |
| Step D | 7 ppm   | 98.4% |      | 0.4% | 1.0 ppm | 0.4 ppm |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as reactants and components to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component, or ingredient as it existed at the time just before it was first contacted, blended or mixed with one or more other substances, components, or ingredients in accordance with the present disclosure. The fact that the substance, component, or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to a substance, component, or ingredient by chemical name or formula exclude the possibility that during the desired reaction itself a substance, component, or ingredient becomes transformed to one or more transitory intermediates that actually enter into or otherwise participate in the reaction. In short, no representation is made or is to be inferred that the named substances, components, or ingredients must participate in the reaction while in their original chemical composition, structure or form.

It will also be understood that the terms "substantially" and "essentially" denote that the subject matter referred to need not involve absolutes. For example, instead of describing a variable operation such as removing water or feeding something "continuously", it is at least equally realistic to describe the operation as being conducted "substantially continuously" as in the practice of this invention it normally makes little if any difference if the operation is temporarily interrupted for a short period of time that does not do material harm to the process. The same is true in the case of doing something "all of the time" or "concurrently" while something else is taking place. It is equally realistic to do that something "substantially all of the time" or "substantially concurrently" while that something else is taking place, as slight interruptions or discontinuities in such things normally will make no material difference in the end result. In short, mathematical precision is not necessary under normal circumstances, and it would be absurd to suggest otherwise. Similarly, it is equally satisfactory to have a liquid phase either as "a single liquid phase" or as "an essentially single liquid phase" or to have something as "an essentially liquid single phase" as well as "a liquid single phase". A little cloudiness or an insignificant amount of another liquid phase in most cases will cause no trouble and thus is acceptable. Since the words "essentially" and "substantially" are words in common usage and that are well-defined in the dictionary, they are deemed sufficiently precise and are thus used herein.

Except as maybe expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of forming an epoxide, which process comprises epoxidizing in a liquid phase, an epoxidizable olefinic compound with hydrogen peroxide in the presence of a catalytic quantity of a tungsten-containing catalyst system, wherein (i) boric acid and (ii) at least one alkanediol individually and/or as a reaction product of (i) and (ii) are being and/or have been included in the liquid phase.

2. A process according to claim 1 wherein said tungsten-containing catalyst system is a tungstate-containing catalyst system.

3. A process according to claim 1 wherein at least one onium compound is being and/or has been included in the liquid phase.

4. A process according to claim 3 wherein said at least one onium compound is at least one quaternary ammonium compound.

5. A process according to claim 3 wherein said tungsten-containing catalyst system is a tungstate-containing catalyst system.

6. A process according to claim 3 wherein said tungsten-containing catalyst system is formed from components comprising (i) tungstic acid or a tungstate salt and an inorganic acid, and wherein said at least one onium compound is at least one quaternary ammonium compound in which each of three substituents on the nitrogen atom contains, independently, six to about sixteen carbon atoms, and the remaining substituent is methyl or ethyl.

7. A process according to claim 6 wherein said each of three substituents is an alkyl group, and wherein said remaining substituent is methyl.

8. A process of forming an epoxide, which process comprises mixing aqueous hydrogen peroxide with at least one epoxidizable olefinic hydrocarbon in the presence of a tungsten-based catalyst in an essentially single phase liquid organic reaction mixture to which (i) boric acid and at least one alkanediol, and/or (ii) a reaction product of (i) and (ii) are added or have been added, and continuously or substantially continuously removing water from the reaction mixture by distillation so that an essentially single-phase liquid reaction mixture is maintained during the reaction.

9. A process according to claim 8 wherein at least one quaternary ammonium salt in which at least substituent on the nitrogen atom is an alkyl group having at least 6 carbon atoms is added or has been added to the reaction mixture.

10. A process according to claim 8 wherein said tungsten-based catalyst is a peroxotungstate catalyst.

11. A process according to claim 10 wherein said peroxotungstate catalyst in the form introduced into the reaction mixture is a preformed peroxotungstate catalyst solution formed from a tungstate salt, an inorganic acid, and aqueous hydrogen peroxide.

12. A process according to claim 11 wherein said tungstate salt is an alkali or alkaline earth metal salt, and wherein said inorganic acid is sulfuric acid.

13. A process according to claim 12 wherein said tungstate salt is sodium tungstate or potassium tungstate, or both.

14. A process according to claim 10 wherein said peroxotungstate catalyst is formed in situ from a tungstate salt, an inorganic acid, and aqueous hydrogen peroxide.

15. A process according to claim 14 wherein said tungstate salt is an alkali or alkaline earth metal salt, and wherein said inorganic acid is sulfuric acid.

16. A process according to claim 15 wherein said tungstate salt is sodium tungstate or potassium tungstate, or both.

17. A process according to claim 8 wherein said concentrated aqueous hydrogen peroxide is at least a 20 wt % aqueous solution of hydrogen peroxide.

18. A process according to claim 8 wherein said concentrated aqueous hydrogen peroxide is at least a 50 wt % aqueous solution of hydrogen peroxide.

19. A process according to claim 8 wherein said at least one olefinic hydrocarbon is at least one alkene hydrocarbon containing in the range of about 5 to about 10 carbon atoms, and wherein said at least one alkanediol has in the range of about 5 to about 10 carbon atoms.

20. A process according to claim 19 wherein said at least one alkene hydrocarbon is a single alkene hydrocarbon, and wherein said at least one alkanediol is a single 1,2-alkanediol having the same number of carbon atoms as said alkene hydrocarbon.

21. A process according to claim 8 wherein at least one tetraalkylammonium halide in which two or three of the alkyl groups substituents on the nitrogen atom each contain independently in the range of 6 to about 12 carbon atoms and each of the one or two other alkyl substituents on the nitrogen atom is independently a methyl or ethyl group is added or has been added to the reaction mixture, wherein said tungsten-based catalyst is a peroxotungstate catalyst, wherein the aqueous hydrogen peroxide used in the reaction is a 5 to 80 wt % aqueous solution of hydrogen peroxide, wherein said at least one olefinic hydrocarbon is at least one 1-alkene hydrocarbon containing in the range of 5 to 8 carbon atoms, and wherein said at least one alkanediol is at least one 1,2-alkanediol having in the range of 5 to 8 carbon atoms.

22. A process according to claim 21 wherein said peroxotungstate catalyst is formed from a tungstate salt, an inorganic acid, and a 20 to 80 wt % aqueous solution of hydrogen peroxide.

23. A process according to claim 22 wherein said peroxotungstate catalyst is a preformed peroxotungstate catalyst.

24. A process according to claim 22 wherein said peroxotungstate catalyst is formed in situ.

25. A process according to claim 22 wherein said tungstate salt is sodium tungstate or potassium tungstate, or both.

26. A process according to claim 25 wherein said inorganic acid is sulfuric acid.

27. A process according to claim 21 wherein said at least one tetraalkylammonium halide is methyl(tri-n-octyl)ammonium chloride, methyl(tri-n-octyl)ammonium bromide, ethyl(tri-n-octyl)ammonium chloride, ethyl(tri-n-octyl)ammonium bromide, di(hexyl)(octyl)methylammonium chloride, di(hexyl)(octyl)methylammonium bromide, tri(dodecyl)methylammonium chloride, or tri(dodecyl)methylammonium bromide, wherein the aqueous hydrogen peroxide used in the reaction is a 50 to 80 wt % aqueous solution of hydrogen peroxide, wherein said at least one olefinic hydrocarbon is 1-hexene, and wherein said at least one 1,2-alkanediol is 1,2-hexanediol.

28. A process according to claim 27 wherein said peroxotungstate catalyst is formed from a tungstate salt and an inorganic acid in the presence of a 50 to 80 wt % aqueous solution of hydrogen peroxide.

29. A process according to claim 28 wherein said tungstate salt is sodium tungstate or potassium tungstate, or both.

30. A process according to claim 29 wherein said inorganic acid is sulfuric acid.

31. A process of forming an epoxide, which process comprises:

A) continuously feeding aqueous hydrogen peroxide solution into a reaction mixture formed from components comprising at least one epoxidizable olefinic compound to which have been added (i-a) tungstic acid and/or (i-b) a tungsten compound and an inorganic acid, (ii) an onium compound, and (iii-a) boric acid and at least one alkanediol and/or (iii-b) a borate ester-containing mixture formed from boric acid and at least one alkanediol, such that at least one epoxide is formed; and B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase.

32. A process according to claim 31 wherein (i-b) is used and in which said tungsten compound is a tungsten (VI) compound.

33. A process according to claim 32 wherein said inorganic acid of (i-b) is sulfuric acid.

34. A process according to claim 31 wherein said onium compound is a quaternary ammonium compound.

35. A process according to claim 31 wherein said olefinic compound is a 1-alkene hydrocarbon, wherein (i-b) is used and in which said tungsten compound is a tungsten (VI) compound, and wherein said at least one alkanediol is at least one 1,2-alkanediol.

36. A process according to claim 35 wherein said inorganic acid of (i-b) is sulfuric acid.

37. A process according to claim 35 wherein said onium compound is a quaternary ammonium compound.

38. A process of forming an epoxide, which process comprises:
   A) continuously cofeeding (1) aqueous hydrogen peroxide solution and (2) at least one olefinic hydrocarbon, into a reaction mixture formed from components comprising (a-1) tungstic acid and/or (a-2) a tungsten compound and an inorganic acid, (b) an onium compound, and (c-1) boric acid and at least one alkanediol and/or (c-2) a borate ester-containing mixture formed from boric acid and at least one alkanediol, such that at least one epoxide is continuously being formed; and
   B) continuously removing water from the reaction mixture by distillation so that at least during substantially the entire time the aqueous hydrogen peroxide is being fed, the reaction mixture has a liquid phase which is a single liquid phase or an essentially single liquid phase.

39. A process according to claim 38 wherein (a-2) is used and in which said tungsten compound is a tungsten (VI) compound.

40. A process according to claim 39 wherein said inorganic acid of (a-2) is sulfuric acid.

41. A process according to claim 38 wherein said onium compound is a quaternary ammonium compound.

42. A process according to claim 38 wherein said olefinic compound is a 1-alkene hydrocarbon, wherein (a-2) is used and in which said tungsten compound is a tungsten (VI) compound, and wherein said at least one alkanediol is at least one 1,2-alkanediol.

43. A process according to claim 42 wherein said inorganic acid of (a-2) is sulfuric acid.

44. A process according to claim 42 wherein said onium compound is a quaternary ammonium compound.

45. A process according to claim 38 wherein said aqueous hydrogen peroxide solution as fed to said reaction mixture contains about 30 to about 70 wt % of hydrogen peroxide, and wherein said olefinic hydrocarbon is a 1-alkene.

46. A process according to claim 40 wherein said onium compound is a quaternary ammonium compound, and wherein (c-1) is used in forming said reaction mixture and in which said boric acid and at least one alkanediol are used without being premixed together.

47. A process according to claim 46 wherein said tungsten (VI) compound is sodium tungstate, wherein said quaternary ammonium compound has at least three hydrocarbyl groups in the molecule at least one of which contains at least 6 carbon atoms, and wherein said at least one alkanediol is a single 1,2-alkanediol.

48. A process according to claim 47 wherein said quaternary ammonium compound has one methyl or ethyl group and three alkyl groups each containing, independently, in the range of 6 to about 12 carbon atoms, wherein said 1,2-alkanediol is 1,2-pentanediol, 1,2-hexanediol, 1,2-heptanediol, or 1,2-octanediol, and wherein said at least one olefinic hydrocarbon is a single linear 1-alkene having the same number of carbon atoms as the alkanediol being used.

49. A process according to claim 48 wherein said linear 1-alkene is 1-hexene and therefore where in said alkanediol is 1,2-hexanediol.

50. A process according to claim 38 wherein during all or substantially all of the time the feeding of (1) and (2) is occurring, the reaction zone is maintained under reflux conditions, such that water, epoxide product, unreacted olefinic hydrocarbon, and some reaction byproducts are continuously or substantially continuously removed from the reaction zone in the form of a vapor stream.

51. A process according to claim 50 wherein epoxide is recovered by operations comprising condensing said vapor stream to form a mixture comprised of water and an organic phase, separating the organic phase from the water, and distilling the epoxide from the organic phase by batch or continuous distillation.

52. A process according to claim 51 wherein unreacted olefinic hydrocarbon is isolated during said distillation and is returned to the reaction mixture.

53. A process according to claim 50 wherein epoxide is recovered by operations comprising feeding said vapor stream to a distillation column, whereby the overhead distillate is composed of unreacted olefinic hydrocarbon and water, separating olefinic hydrocarbon and water from each other by a liquid-liquid phase separation, returning the separated olefinic hydrocarbon to the reaction mixture, and recovering epoxide as bottoms from the distillation column.

54. In a tungsten-based catalyzed epoxidation reaction, the improvement which comprises including (i) boric acid and an alkanediol or (ii) a borate ester formed therefrom, or (iii) both of (i) and (ii) in the epoxidation reaction mixture.

55. The improvement according to claim 54 wherein said alkanediol is a 1,2-alkanediol having in the range of about 5 to about 10 carbon atoms.

56. In a peroxotungstate-catalyzed epoxidation reaction, the improvement which comprises introducing into the epoxidation reaction mixture (i) boric acid and an alkanediol or (ii) a borate ester formed from boric acid and an alkanediol, or (iii) both of (i) and (ii).

57. The improvement according to claim 56 wherein said alkanediol is a 1,2-alkanediol having in the range of about 5 to about 10 carbon atoms.

58. A process which comprises mixing together (i) hydrogen peroxide, (ii) at least one 1-alkene, (iii) at least one quaternary ammonium salt wherein at least one of the substituents on the nitrogen atom is an alkyl group containing at least six carbon atoms, (iv) a 1,2-alkanediol and boric acid; and (v) a preformed catalyst solution formed from hydrogen peroxide, at least one aqueous inorganic acid, and at least one tungstate salt, while removing water, such that a 1,2-epoxide is formed.

59. A process for the epoxidation of a 1-alkene, which process comprises concurrently, or substantially concurrently, feeding into a reaction zone:
   (a) hydrogen peroxide,
   (b) at least one 1-alkene, and
   (c) at least one quaternary ammonium salt wherein at least one of the substituents contains at least six carbon atoms,
said (b) and (c) being fed individually and/or in combination; wherein boric acid or both a 1,2-diol and boric acid are present in said reaction zone prior to the initiation of said feeding, and wherein a preformed catalyst solution formed from hydrogen peroxide, at least one aqueous inorganic acid, and at least one tungstate salt is present in said reaction zone prior to the initiation of said feeding, such that said reaction zone is maintained under reflux conditions during all or substantially all of the time said feeding is occurring; such that water is continuously or substantially continuously removed from the reaction zone; and such that an epoxide is formed, which epoxide is distilled from the reaction zone.

60. A process according to claim 59 wherein (i) is a solution in the range of about 30 wt % to about 75 wt % of hydrogen peroxide in water; wherein (b) and (c) are fed in combination; and wherein more preformed catalyst solution of tungstate is intermittently added to the reaction zone.

* * * * *